United States Patent
Babcock et al.

[11] 3,937,827
[45] Feb. 10, 1976

[54] THERAPEUTIC COMPOSITION AND METHOD OF TREATING ADVANCED OR DISSEMINATED MAMMARY CANCER

[75] Inventors: John C. Babcock; Roman P. Holysz, both of Kalamazoo, Mich.

[73] Assignee: The Upjohn Company, Kalamazoo, Mich.

[22] Filed: Aug. 30, 1974

[21] Appl. No.: 501,885

Related U.S. Application Data

[63] Continuation-in-part of Ser. No. 393,851, Sept. 4, 1973, abandoned, which is a continuation-in-part of Ser. No. 160,900, July 8, 1971, abandoned, which is a continuation of Ser. No. 855,050, Sept. 3, 1969, abandoned, which is a continuation-in-part of Ser. No. 823,490, May 9, 1969, abandoned.

[52] U.S. Cl. .............................................. 424/243
[51] Int. Cl.². ....................................... A61K 31/56
[58] Field of Search .................................... 424/243

Primary Examiner—Jerome D. Goldberg
Attorney, Agent, or Firm—John J. Killinger; Roman Saliwanchik

[57] ABSTRACT

Compounds of the formula:

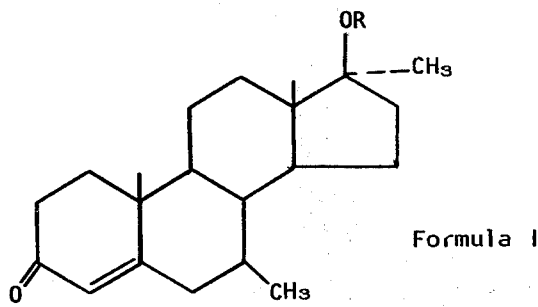

Formula I wherein R is hydrogen prepared in unit dosage form with appropriate pharmaceutical carrier for oral and parenteral administration and process of producing regression in subjects with advanced or disseminated mammary cancer in woman.

1 Claim, No Drawings

THERAPEUTIC COMPOSITION AND METHOD OF TREATING ADVANCED OR DISSEMINATED MAMMARY CANCER

CROSS REFERENCE TO RELATED APPLICATIONS

This application is a continuation-in-part of copending application Ser. No. 393,851, filed Sept. 4, 1973, now abandoned which in turn is a continuation-in-part of application Ser. No. 160,900, filed July 8, 1971 (now abandoned), which in turn is a continuation of application Ser. No. 855,050, filed Sept. 3, 1969 (now abandoned), which in turn is a continuation-in-part of application Ser. No. 823,490, filed May 9, 1969 (now abandoned).

BRIEF SUMMARY OF THE INVENTION

This invention relates to new and useful pharmaceutical compositions, in unit dosage form, comprising a compound of the formula:

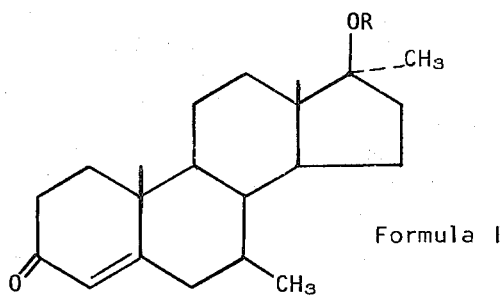

Formula I

It has been found in accordance with the present invention that regression of advanced or disseminated mammary cancer can be obtained in human subjects by the systemic administration of a compound of the Formula I. The term advanced or disseminated mammary cancer is used to designate a general class of treatable tumors whether or not a particular patient has responded previously to hormonal therapy with steroid agents, nonsteroidal hormonal agents, or ablative procedures. Advantageously the administration of a compound of the Formula I in women does not provoke significant virilizing side effects such as acne, hirsutism, increased libido or clitoral enlargement.

The following Table I is a tabulation of eight human females treated with $7\beta,17\alpha$-dimethyltestosterone. The Response* is evaluated in accordance with criteria developed by The Cooperative Breast Cancer Group (Cooperative Breast Cancer Group: Protocol 1 — A cooperative study to evaluate experimental steroids in the therapy of advanced breast carcinoma. Cancer Chemo, Rpts. 11). A regression is called only if measurable tumor masses shrink, osteolytic lesions recalcify, and there are no lesions during the treatment period. An additional requirement is that the regression must be concurred in by two extramural examiners who review X-ray films, photographs and measurements without knowning which patient received which compound.

$7\beta,17\alpha$-Dimethyltestosterone is also known by the code number U-22,550.

TABLE 1

$7\beta,17\alpha$-dimethyltestosterone as Late Hormonal Therapy in Advanced Breast Cancer
(3.4 mg./kg./day by mouth for 6 weeks to 9 months)

| Pt. | Age | Maestec-tomy | Site of Metastasis | Previous Treatment | Previous Treatment Response | $7\beta,17\alpha$-dimethyltestosterone Dose mg./day | Response* |
|---|---|---|---|---|---|---|---|
| 1. | 53 | 1962 | Osseous | Castration Cortisol | Regression " | 250 | Osseous Regression |
| 2. | 63 | 1966 | Osseous | Cortisol + triiodothyronine Stilbestrol | Failure " | 250 | Osseous Regression |
| 3. | 63 | 1963 | Osseous | Stilbestrol Ethynyl estradiol | Failure " | 250 | Osseous Regression |
| 4. | 57 | 1959, 1967 | Visceral: lung | Stilbestrol | Failure | 200 | Pulmonary Regression |
| 5. | 58 | 1966 | Visceral: RLQ mass Osseous | Delatestryl Chlorambucil | Failure " | 200 | Visceral & Osseous Regression |
| 6. | 54 | 1954, 1957 | Visceral: Pleural Osseous | Stilbestrol | Failure | 200 | Osseous Regression |
| 7. | 53 | 1963 | Osseous | $\Delta^1$-testololactone Testosterone propionate 5-Fluorouracil | Failure " " | 150 | Osseous Regression (Unreviewed) |
| 8. | 52 | 1961 | Osseous | Cortisol + Triiodothyronine | Failure | 300 | Osseous Regression (Unreviewed) | wherein R is hydrogen in association with a pharmaceutical carrier. The invention also encompasses a process for producing regression of advanced or disseminated mammary cancer by administering to said subjects the foregoing compositions.

DETAILED DESCRIPTION

The term androstane is used herein to designate $5\alpha$-androstane.

The compound can be prepared following the instructions in U.S. Pat. No. 3,262,949. $7\beta,17\alpha$-dimethyltestosterone ($7\beta,17\alpha$-dimethylandrost-4-ene-$17\beta$-ol-3-one) is prepared according to Example 15 of U.S. Pat. No. 3,262,949.

The compositions of the present invention are presented for administration to humans and animals in unit dosage forms, such as tablets, capsules, pills, powders, granules, sterile parenteral solutions or suspensions, and oral solutions or suspensions, and oil-water emulsions containing suitable quantities of the compound of Formula I.

For oral administration either solid or fluid unit dosage forms can be prepared. For preparing solid compositions such as tablets, the compound of Formula I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Wafers are prepared in the same manner as tablets, differing only in shape and the inclusion of sucrose or other sweetener and flavor. In their simplest embodiment, capsules, like tablets, are prepared by mixing the steroid with an inert pharmaceutical diluent and filling the mixture into a hard gelatin capsule of appropriate size. Soft gelatin capsules are prepared by machine encapsulation of a slurry of the steroid with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar and saccharin, together with an aromatic flavoring agent.

Suspensions can be prepared with a syrup vehicle with the aid of a suspending agent such as acacia, tragacanth, methylcellulose and the like.

For parenteral administration, fluid unit dosage forms are prepared utilizing the steroid and a sterile vehicle, water being preferred. The steroid, depending on the vehicle and concentration used, can be either suspended or dissolved in the vehicle. In preparing solutions the steroid can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized power is then sealed in the vial and an accompanying vial of water for injection is supplied to reconstitute the liquid prior to use. Parenteral suspensions are prepared in substantially the same manner except that the steroid is suspended in the vehicle instead of being dissolved and sterilization cannot be accomplished by filtration. The steroid can be sterilized by exposure to ethylene oxide before suspending in the sterile vehicle. Advantageously, a surfactant or wetting agent is included in the composition to facilitate uniform distribution of the steroid.

The term unit dosage form as used in the specification and claims refers to physically discrete units suitable as unitary dosages for human subjects and animals, each unit containing a predetermined quantity of active material calculated to produce the desired therapeutic effect in association with the required pharmaceutical diluent, carrier, or vehicle. The specifications for the novel unit dosage forms of this invention are dicated by and directly dependent on (a) the unique characteristics of the active material and the particular therapeutic effect to be achieved, and (b) the limitations inherent in the art of compounding such an active material for therapeutic use in humans and animals, as disclosed in detail in this specification, these being features of the present invention. Examples of suitable unit dosage forms in accord with this invention are tablets, capsules, pills, suppositories, powder packets, granules, wafers, cachets, teaspoonfuls, tablespoonfuls, dropperfuls, ampuls, vials, segragated multiples of any of the foregoing, and other forms as herein described.

The dosage of the steroid for treatment depends on route of administration; the age, weight, and condition of the patient; and the particular disease to be treated. A daily dosage of from about 150 to 300 mg., in single or divided doses, embraces the effective range for treatment. The dosage is calculated on the basis of from about 1 to about 50 mg./kg. by weight of subject to be administered daily, although for injectable dosage forms, less frequent administration, e.g., 1 to 3 times per week, is preferred.

The steroid is compounded with a suitable pharmaceutical carrier in unit dosage form for convenient and effective administration. In the preferred embodiments of this invention, the dosage units contain the steroid in 50, 100, 200 and 500 mg. amounts for systemic treatment; and 5 to 25% w/v for parenteral treatment. The dosage of compositions containing a compound of Formula I and one or more other active ingredients is to be determined with reference to the usual dosage of each such ingredient.

In addition to the administration of a compound of Formula I as the principal active ingredient of compositions for treatment of the conditions described herein, the said compound can be combined with other compounds to obtain advantageous combinations of properties. Such combinations include a compound of Formula I with thiotepa (20–60 mg.), chlorambucil (0.03–0.2 mg./kg.), cyclophosphamide (2.5–40 mg./kg.), fluorouracil (6–12 mg./kg.), vinblastine sulfate (0.1–0.5 mg./kg.), and dromostanolone propionate (50–100 mg. three times a week).

A compound of the Formula I, alone or in combination with one of the above drugs can also be administered at the time of mastectomy or other surgical procedure.

The following examples are illustrative of the best mode contemplated by the inventors for carrying out their invention and are not to be construed as limiting.

EXAMPLE 1

A lot of 10,000 tablets, each containing 50 mg. of $7\beta,17\alpha$-dimethyltestosterone is prepared from the following types and amounts of ingredients:

| | |
|---|---|
| $7\beta,17\alpha$-dimethyltestosterone, micronized | 500 gm. |
| Dicalcium phosphate | 1,500 gm. |
| Methylcellulose, U.S.P. (15 cps.) | 60 gm. |
| Talc | 150 gm. |
| Corn starch | 200 gm. |
| Calcium stearate | 12 gm. |

The steroid and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and stearate, and compressed into tablets.

These tablets are useful in the treatment of breast cancer at a dose of 1 tablet 4 times a day to post-menopausal woman with advanced or disseminated mammary cancer.

EXAMPLE 2

One-thousand two-piece hard gelatin capsules, each containing 250 mg. of $7\beta,17\alpha$-dimethyltestosterone are prepared from the following types and amounts of ingredients:

| | |
|---|---|
| $7\beta,17\alpha$-dimethyltestosterone, micronized | 250 gm. |
| Talc | 25 gm. |
| Magnesium stearate | 2.5 gm. |

The ingredients are mixed well and filled into capsules of the proper size.

Capsules so prepared are useful in the initial treatment of breast cancer at a dose of one capsule 4 times a day.

EXAMPLE 3

One-thousand tablets for sublingual use are prepared from the following ingredients:

| | |
|---|---|
| 7β,17α-dimethyltestosterone, micronized | 50 gm. |
| Polyethylene glycol, 4,000 powdered | 150 gm. |
| Polyethylene glycol, 6,000 powdered | 75 gm. |

The ingredients are mixed well and compressed into sublingual-type tablets weighing 275 mg.

These tablets placed under the tongue are useful in the treatment of advanced or disseminated mammary cancers at a dose of 1 tablet 3 times a day.

EXAMPLE 4

Soft gelatin capsules for oral use, each containing 25 mg. of 7β,17α-dimethyltestosterone, are prepared by first dispersing the micronized steroid in corn oil to render the material capsulatable and then encapsulating in the usual manner.

One or two capsules taken 4 times a day are useful in the treatment of breast cancer.

EXAMPLE 5

1,000 Tablets, each containing 50 mg. of 7β,17α-dimethyltestosterone are made from the following types and amounts of ingredients:

| | |
|---|---|
| 7β,17α-dimethyltestosterone | 50 gm. |
| Lactose | 360 gm. |
| Microcrystalline cellulose NF | 120 gm. |
| Starch | 16 gm. |
| Magnesium stearate powder | 4 gm. |

The ingredients are screened and blended together and pressed into 550 mg. tablets.

The tablets are useful in the treatment of advanced breast cancer subsequent to mastectomy at a dose of from 3 to 6 tablets daily.

EXAMPLE 6

A sterile preparation suitable for intramuscular injection and containing 50 mg. of 7β,17α-dimethyltestosterone in each milliliter is prepared from the following ingredients:

| | |
|---|---|
| 7β,17α-dimethyltestosterone | 50 gm. |
| Benzyl benzoate | 200 ml. |
| Methylparaben | 1.5 gm. |
| Propylparaben | 0.5 gm. |
| Cottonseed oil q.s. | 1,000 ml. |

One milliliter of this sterile preparation is injected once a day in the treatment of advanced or disseminated mammary cancers.

EXAMPLE 7

A sterile preparation suitable for intramuscular injection and containing 50 mg. of 7β,17α-dimethyltestosterone in each milliliter is prepared from the following ingredients:

| | |
|---|---|
| 7β,17α-dimethyltestosterone, sterile micronized | 50 gm. |
| Polyethylene glycol, 4,000 | 30 gm. |
| Sodium chloride | 9 gm. |
| Polysorbate 80 | 4 gm. |
| Benzyl alcohol | 9 gm. |
| Water for injection q.s. | 1,000 ml. |

The polyethylene glycol, sodium chloride, polysorbate 80 and benzyl alcohol are dissolved in the water and the solution sterilized by passage through a sterilizing filter. Sterile 7β,17α-dimethyltestosterone is then mixed aseptically with the sterile vehicle. The suspension is filled aseptically into sterile 2 milliliter ampuls.

Two milliliters of this suspension injected intramuscularly once every other day is useful in the treatment of advanced or disseminated mammary cancers.

We claim:

1. A process for producing regression of advanced or disseminated mammary cancer comprising the oral or parenteral administration of 7β,17α-dimethyltestosterone in association with a pharmaceutical carrier to an adult woman with advanced or disseminated mammary cancer, wherein from about 1 to about 50 mg. of compound selected per kg. of said adult woman's weight/day is administered.

* * * * *